US00PP20442P3

(12) United States Plant Patent
Fang

(10) Patent No.: US PP20,442 P3
(45) Date of Patent: Oct. 27, 2009

(54) ***BEALLARA* BIG SHOT 'HILO SPARKLE'**

(50) Latin Name: *Beallara*
Varietal Denomination: Hilo Sparkle

(76) Inventor: James Yen Jen Fang, HC1 Box 9, Mountain View, HI (US) 96771

( * ) Notice: Subject to any disclaimer, the term of this patent is extended or adjusted under 35 U.S.C. 154(b) by 0 days.

(21) Appl. No.: 12/005,248

(22) Filed: Dec. 21, 2007

(65) Prior Publication Data

US 2009/0165179 P1 Jun. 25, 2009

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para
*Assistant Examiner*—Louanne C Krawczewicz Myers

(57) ABSTRACT

A new variety of orchid plant of the Oncidiinae Intergenerics, *Beallara,* named *Beallara* Big Shot 'Hilo Sparkle', distinguished particularly by a clean striking color and large star-shaped flowers that are arranged pleasingly on a raceme and growing quickly to sexual maturity.

2 Drawing Sheets

Latin name of the genus and grex of the plant claimed: The Latin name of the genus and grex of the plant claimed is *Beallara* Big Shot.

Variety denomination: The present invention comprises a new and distinct cultivar of *Beallara* orchid, and hereinafter referred to by the cultivar name *Beallara* Big Shot 'Hilo Sparkle'.

BACKGROUND OF THE INVENTION

*Beallara* is an artificial hybrid of orchids between four genera in the subtribe Oncidiinae. *Beallara* is made from the genera *Odontoglossum,* consisting of about 300 species, *Brassia,* consisting of a little over 30 species, *Miltonia,* consisting of about 11 species of the 'Brazilian *Miltonias'* (intermediate to warm growing, distinguished from the cool growing '*Miltoniopsis'*) and *Cochlioda,* consisting of 6 species. The first hybrid of *Beallara* was created in 1970 by Beall and registered by Moir. Due to the varying percentages of the parent genera that make up *Beallara* and the gene expression in their progeny, *Beallara* varies in morphology and size. All exhibit sympodial growth habit.

*Beallara* breeding is typically done from sexual methods. Asexual propagation of *Beallara* is often done in aseptic tissue culture from apical or axillary shoots at a tissue culture laboratory.

The new cultivar was discovered within the progeny of a cross made in Hilo, Hi. on Dec. 4, 2001. The Inventor selected *Beallara* Big Shot 'Hilo Sparkle' as a single plant from a population of over 100 plants grown in Mountain View, Hi. *Beallara* Big Shot 'Hilo Sparkle' was re-flowered for evaluation and submitted by the Inventor to a commercial tissue culture laboratory in Bangkok, Thailand on Mar. 3, 2007 for asexual propagation through aseptic tissue culture technique.

Other seedlings from the same cross that was used to produce *Beallara* Big Shot 'Hilo Sparkle' have been commercially available from others. The characteristics of *Beallara* Big Shot 'Hilo Sparkle' are clearly distinguishable from the characteristics of its silblings. The sibling plants were sold without specific epithet to individuals and other nurseries. To the Inventor's knowledge, there are no other named clones of the cross. The inventor has reason to believe that *Beallara* Big Shot 'Hilo Sparkle' is superior to the other seedlings in flower size, shape and color as well as the spiking habit. Plants of the grex *Beallara* Big Shot are sold as plants of the grex without specific epithet.

BRIEF SUMMARY OF THE INVENTION

The following traits have been repeatedly observed and are determined to be basic characteristics of the new cultivar which in combination distinguish this *Beallara* orchid as a new and distinct cultivar:

Flowers of the new cultivar are creamy white in color with irregular purple blotches on the basal half of the sepals and petals. The labellum is creamy white with a broad maroon blotch surrounding the callus. The callus is yellow overlaid with maroon striate and develops as a swelling in the lip throat, bifurcating into two diverging horns about 5 millimeters (mm) in height. The anther cap and column are creamy white in color. The sides of the column are overlaid by purple towards the base and the underside of the column becomes yellow towards the base. The column wings are rectangular denticulate, mainly creamy white in color with a small purple spot. The flowers are rigid and slightly scented. The natural horizontal spread is 12.2 centimeters (cm); natural vertical spread is 12.9 cm; dorsal sepal width 2.5 cm; dorsal sepal length 7.0 cm; petal width 3.0 cm; petal length 6.9 cm; lateral sepal width 2.3 cm; lateral sepal length 6.8 cm; labellum width 6.5 cm; labellum length 6.1 cm. The plant produces one inflorescence on the first bloom with six flowers.

Inflorescence is a basal raceme, upright or arching, and approximately 38–58 cm tall. The plant is relatively compact and the size of the inflorescence is appropriate to the overall size of the plant and typical pot size for this cultivar.

There are generally four leaves on the mature psuedobulb, two from the apex and two from the base of the psuedobulb. The apical leaves measure around 20 to 36 cm long and are around 4 to 5 cm wide. The leaves from the base of the pseudobulb measure from 19.5 to 25.5 cm long and are 4.5 to 5.5 cm wide. Axillary leaves, or bracts, are usually present below the leaves at the base of the psuedobulb. When present, there is usually one on either side of the pseudobulb, 7 to 15 cm long, appearing as a sheath. The leaves are lanceolate acuminate, entire and semi-conduplicate at the base. The texture and substance is slightly undulate, waxy and somewhat coriaceous. The plants of *Beallara* Big Shot 'Hilo Sparkle' grow to maturity and flower in approximately 18 months.

Plants of the new cultivar have not been observed under all possible environmental conditions. The phenotype may vary significantly with variations in the environment such as temperature, light intensity, and day length, without however any change in genotype.

Plants of the new cultivar differ primarily from the plants of the parent cultivars in flower color, panicle size, rate of growth and speed to maturation. Perhaps the closest commercial comparison to the new cultivar can be made to seedling-derived *Beallara* orchids which are genetically heterogeneous, and typically lack uniformity in growth, vigor, plant habit, and flower quality. Since this reference point has inconsistent characteristics, a direct comparison for *Beallara* Big Shot 'Hilo Sparkle' is not available. The new cultivar is a single genotype asexually propagated via tissue culture; thus, its combined horticultural characteristics listed above are uniform and predictable.

BRIEF DESCRIPTION OF THE DRAWINGS

The drawings show the colors of the new variety as nearly true as possible with an illustration of this type. In the drawings.

DETAILED BOTANICAL DESCRIPTION

Figure 1:
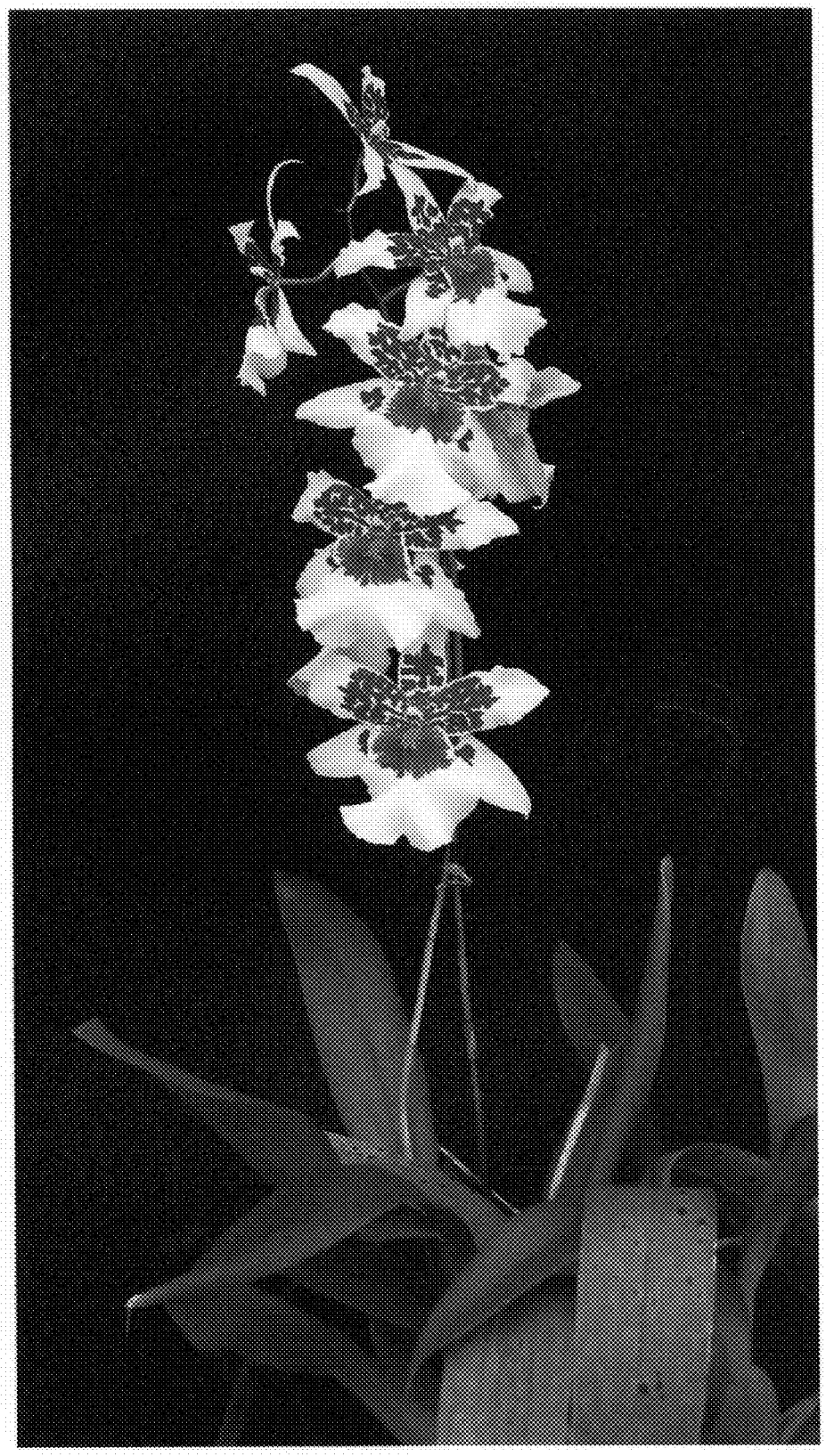
FIG. 1 is a view of the entire plant to reveal the growth habit and general characteristics with its flowers, which is typical of this new variety.
Figure 2:
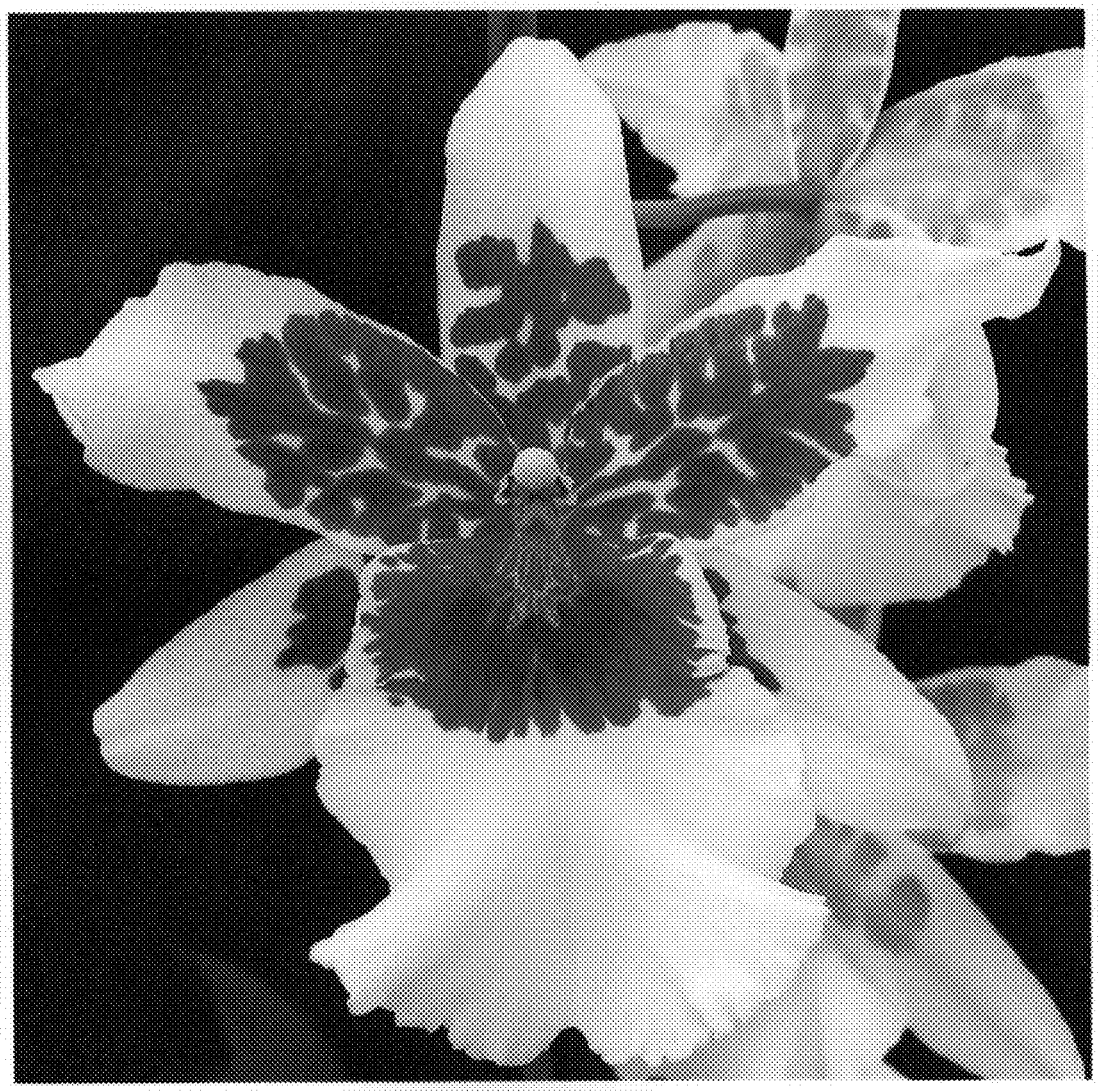
FIG. 2 is a close up view of the flower to show its shape.

All color references are measured against the Pantone® Color System. Colors and numerical measurements are approximate as plant growth and development depends on environmental conditions and cultural practices such as light level, temperature, water quality, fertilization formula and rate, among others, without, however, any variance in genotype.

Plants used for this description are 18 months in vivo and grown in square, black plastic pots measuring 3.5" at the top of the pot and tapering down to 2.5" at the bottom of the pot with a height of 3.75", grown in a poly-film covered greenhouse in Mountain View, Hi., where day temperatures range from 75 to 85 degrees and night temperatures range from 55 to 65 degrees Fahrenheit. Light levels are approximately 2500 foot candles. This information reflects the annual variations for the area.

Botanical classification: *Beallara* Big Shot 'Hilo Sparkle'.

Parentage: Seedling selected from the cross of the following:

*Seed parent.*—*Miltonia* Maui Titan.

*Pollen parent.*—*Beallara* Tahoma Glacier.

Propagation:

*Type.*—Asexual propagation by aseptic tissue culture through axillary shoot initiation.

*Time to initiate and elongate roots in-vivo.*—About 45 days.

*Time to produce fully rooted young plant.*—About 240 days.

Root description: Velamen covered roots, approximately 2 mm in diameter, white in color with yellow to green growing tip. The exact shades of white and yellow/green vary greatly with minimal changes in environmental conditions.

Plant description: Under appropriate growing conditions, plants of the new cultivar attain a mature size of about 36 cm in height (top of leaf plane) and about 5.0 cm in width. The height from soil level to the top of the inflorescences averages 42.5 cm.

Foliage description:

*Arrangement.*—Sympodial growth habit.

*Quantity of leaves per growth.*—Each sympodial growth has shown four leaves, two on the apex of the pseudobulb and two from the axis at the base of the pseudobulb.

*Leaf length.*—Leafs measure up to 36 cm in length. The axillary leaves at the base of the psuedobulb may be as short as 7 cm to appear to be a sheath and as long as 15 cm.

*Leaf width.*—The width of the largest leaf measures up to 5.0 cm.

*Leaf shape.*—The shape is lanceolate acuminate, entire, apex acute and slightly recurved with a semi-conduplicate base. The leaf margins are smooth, parallel venation apparent, texture and substance of both the upper and lower surfaces of the leaf is slightly undulate, waxy and coriaceous.

*Pseudobulb shape.*—The pseudobulb shape is a laterally compressed ovoid.

*Pseudobulb length.*—The pseudobulb is approximately 8 to 11.5 cm long.

*Psuedobulb width.*—The pseudobulb is approximately 5 cm wide and 1.5 cm thick.

*Foliage color.*—Under the described growing conditions, the foliage color on both sides of the leaves is similar to Pantone® 371C (green) of the Pantone® Color System. There is no vein color distinction. The pseudobulb color ranges from Pantone® 5825C (yellowish green) to Pantone® 371C (green).

Flower/inflorescence description:

*Description.*—Upright or arching raceme, terete, approximately 38 cm in length and 0.4 cm in width on a first bloom plant, typically occurring on the second psuedobulb and grown in square black plastic pots measuring 3.5" on top, 2.5" on the bottom with a height of 3.75". The glabrous peduncles range from approximately 10–15 cm in length with a diameter of 0.03–0.05 cm and the coloration is light green (Pantone 377PC). The pedicels are approximately 5.3 cm in length and 0.03 cm in diameter. Although somewhat pliable when physically bent, they are fairly rigid and strong, supporting each flower sufficiently. The angle of the pedicels are 45° or less when the plant is in bud, changing to a 75–90° angle when the flowers open, giving the flowers proper spacing to display themselves without overcrowding. The texture of the pedicels is rugose and the coloration is light green (Pantone® 377PC). Each raceme averages 6 flowers. Typically, there is one inflorescence per psuedobulb, but at times, two inflorescences per pseudobulb have been observed on this cultivar. The flowers begin approximately halfway up the raceme and are spaced around 3 to 4 cm apart. The size of the inflorescence is appropriate to the overall size of the plant and typical pot size for this cultivar. The above description is of a first bloom plant in the pot sized as outlined with 2 pseudobulbs. If additional pseudobulbs are grown, each psuedobulb will produce 1–2 racemes with and average of 6 flowers.

The flower buds are conical acute, 1 cm in diameter and 4 cm in length. The surface is glabrous and the coloration is Pantone® 381UP (light green) and Pantone® 254UP (purple).

The flowers are bilaterally symmetrical, which is typical of most orchids. Each flower consists of 3 sepals and 3 petals. The lower petal is modified and referred to as the labellum and/or lip. The dorsal sepal is lanceolate, apex apiculate and reflexed, margins smooth. The lateral sepals are similar in shape though slightly smaller in length and width. The base of the sepals is mainly hidden by the overlapping of the petals at this junction. Petals are ovate acuminate, apex reflexed with somewhat undulate margins and slightly concave at the base. Sepal and petal texture is crystalline and hyaline, which allows you to see the parallel venation. The sepals and petals are creamy white in color (Pantone® 7499C). The basal half of the sepals and petals is marked with heavy maroon/purple (Pantone® 242C) blotching. The lower surfaces of the sepals and petals is similar, these colors faded but showing through, except for the mesial parts of the sepals which are light green (Pantone® 380UP) from the base to the apex and approximately 0.7 cm wide. The labellum (lip) is a compressed ovoid, bilobed with undulate margins. The lip lamina is almost square shaped at its base. The texture of both upper and lower surfaces is crystalline and pannose. The main color is creamy white (Pantone® 7499C). The callus is yellow and maroon as described below. Outside of the callus is a broad patch, darker maroon towards the base (Pantone® 696PC ) and lighter maroon (Pantone® 696C) towards the margins.

The callus of the labellum begins at its base as a swelling and extends mesially towards the apex. The callus diverges into two horns pointing down and slightly outward, 5 mm in height, 1.3 cm in length, and each approximately 0.5 cm in width. The texture of the apical surfaces of the calli are dentate, the sides are rigid and smooth. The color for all surfaces of the callus is yellow (Pantone® 7405C) with maroon (Pantone® 696C) striations.

*Dimensions.*—Flower dimensions are: natural horizontal spread is 12.2 cm; natural vertical spread is 12.9 cm; dorsal sepal width is 2.5 cm; dorsal sepal length is 7.0 cm; lateral sepal width is 2.3 cm; lateral sepal length is 6.8 cm; petal width is 3.0 cm; petal length is 6.9 cm; labellum width is 6.5 cm; labellum length is 6.1 cm.

*Coloration.*—The dominant flower color that appears on the sepals and petals as well as the labellum is a creamy white, Pantone® 7499C. The interior irregular blotching of the tepals is purple Pantone® 242C. The broad maroon blotch surrounding the callus ranges from Pantone® 696C around the edges to Pantone® 696PC on the interior. The crest of the labellum is yellow, Pantone® 7405C, striated maroon, Pantone® 696C. The anther cap is creamy white, Pantone® 7499PC. The base color of the column is creamy white, with purple, Pantone® 242C, on the sides towards the base and yellow, Pantone® 7405C, on the underside towards the base. The pollinia are completely concealed by the anther cap, and if it is removed the pollinia may be extracted. The pollinia are yellow, Pantone® 116U, but can range in shades of yellow as the plant ages.

Quantity of flowers and time to flower:

*Flower longevity.*—The flowers can last longer than 8 weeks on the plant with good environmental conditions. A first bloom plant will produce around 6 flowers depending on environmental conditions. Since this plant has been grown for pot plant purposes, cut flower longevity has not been observed.

*Natural flowering season.*—This plant has appeared to be free flowering although the dominant flowering season is fall (September, October, November, December).

Fragrance: A slight fragrance has been detected by the Inventor.

Reproductive organs: The stamens, style and stigmas are fused into a single short structure called the column, possessing one terminal anther with pollen grains united to a pollinia, which are covered by an anther cap. The stigma is located under the column behind the pollinia. The ovary is inferior, with three carpels being present.

*Column.*—The column is erect with rectangular denticulate wings on either side of the stigma, 2 mm wide by 5 mm long.

*Pollinia.*—Two oval masses of pollen are present, about 1 mm in diameter and 2 mm long.

*Stigma.*—The stigma is concave, round, with a high gloss, and sticky. The length of the stigma is 1.3 cm and the width is 0.3 cm. The stigma is cream colored (Pantone® 614PC).

*Ovary.*—The ovary is about 5.5 cm long by 4 mm in diameter and light green in color (Pantone® 377PC).

*Seed.*—Seed production has not been observed.

Disease resistance: Resistance or susceptibility to known pathogens of *Beallara* has not been observed on plants grown under commercial production conditions.

General observations: Plants of *Beallara* Big Shot 'Hilo Sparkle' produce a pleasing arrangement of large, creamy white, star-shaped flowers with a clean striking color on a raceme that is desirable in size for the size of the plant. The flowers are long lasting and nicely shaped. The plant grows quickly to sexual maturity.

What is claimed is:

1. A new and distinct variety of orchid plant named *Beallara* Big Shot 'Hilo Sparkle', substantially as illustrated and described herein.

* * * * *